US010537143B2

(12) United States Patent
Guenther et al.

(10) Patent No.: US 10,537,143 B2
(45) Date of Patent: Jan. 21, 2020

(54) WORKWEAR UNIT HAVING A GLOVE THAT FASTENS A CONTROL SYSTEM AND FUNCTIONAL MODULE TO A USER'S BODY

(71) Applicant: WORKAROUND GMBH, Munich (DE)

(72) Inventors: Paul Guenther, Bad Teinach-Zavelstein (DE); Jonas Girardet, Munich (DE); Thomas Kirchner, Munich (DE); Alexander Grots, Munich (DE)

(73) Assignee: Workaround GmbH (DE)

( * ) Notice: Subject to any disclaimer, the term of this patent is extended or adjusted under 35 U.S.C. 154(b) by 538 days.

(21) Appl. No.: 14/880,456

(22) Filed: Oct. 12, 2015

(65) Prior Publication Data

US 2016/0161301 A1 Jun. 9, 2016

(30) Foreign Application Priority Data

Oct. 11, 2014 (DE) .......................... 10 2014 015 082
Jul. 15, 2015 (DE) .......................... 10 2015 111 506

(51) Int. Cl.
| | |
|---|---|
| *A41D 19/00* | (2006.01) |
| *A61B 5/00* | (2006.01) |
| *G01D 11/30* | (2006.01) |
| *G09B 19/00* | (2006.01) |
| *H01R 24/76* | (2011.01) |

(52) U.S. Cl.
CPC .......... *A41D 19/0027* (2013.01); *A61B 5/681* (2013.01); *A61B 5/6806* (2013.01); *A61B 5/6824* (2013.01); *A61B 5/6825* (2013.01); *A61B 5/6826* (2013.01); *G01D 11/30* (2013.01); *G09B 19/00* (2013.01); *H01R 24/76* (2013.01)

(58) Field of Classification Search
CPC ..... A61B 5/6806; A61B 5/681; A61B 5/6824; A61B 5/6825; A61B 5/6826; A41D 19/0027
See application file for complete search history.

(56) References Cited

U.S. PATENT DOCUMENTS

| | | | |
|---|---|---|---|
| 2010/0023314 A1* | 1/2010 | Hernandez-Rebollar | ................... G06F 3/014 704/3 |
| 2010/0090949 A1* | 4/2010 | Tianqiao | ................. G06F 3/014 345/158 |

(Continued)

OTHER PUBLICATIONS

Borghetti M. et al., "Sensorized Glove for Measuring Hand Finger Flexion for Rehabilitation Purposes," IEEE Transactions on Instrumentation and Measurement, vol. 62, No. 12, Dec. 2013.*

(Continued)

*Primary Examiner* — Michael Jung
(74) *Attorney, Agent, or Firm* — Carlson, Gaskey & Olds, P.C.

(57) ABSTRACT

A workwear unit for detecting, documenting, analyzing, monitoring and/or teaching processes has a portable control system and at least one functional module that is detachably connected with the control system. The functional module comprises at least a sensor module and/or a peripheral device. The unit includes at least a glove and/or a bracelet which can be worn on the hand or on the arm and fastens the control system and/or the functional module to the user's body.

33 Claims, 13 Drawing Sheets

(56) References Cited

U.S. PATENT DOCUMENTS

| | | | | |
|---|---|---|---|---|
| 2010/0234182 | A1* | 9/2010 | Hoffman | A61B 5/1125 482/8 |
| 2012/0025945 | A1* | 2/2012 | Yazadi | H04L 67/1095 340/4.2 |
| 2012/0157263 | A1* | 6/2012 | Sivak | G06F 3/014 482/4 |
| 2013/0258644 | A1* | 10/2013 | Comunale | A41D 19/0157 362/103 |
| 2014/0125577 | A1* | 5/2014 | Hoang | G06F 3/017 345/156 |
| 2015/0257733 | A1* | 9/2015 | Corbett, III | A61B 8/4455 600/440 |
| 2015/0314195 | A1* | 11/2015 | Bekri | A63F 13/245 463/30 |
| 2015/0375042 | A1* | 12/2015 | Schaffer | A61B 5/1116 482/8 |
| 2016/0018901 | A1* | 1/2016 | Woolley | G06F 3/017 345/156 |
| 2016/0284236 | A1* | 9/2016 | Bavunoglu | G09B 21/00 |
| 2017/0119553 | A1* | 5/2017 | Cipriani | A61F 2/68 |
| 2017/0296098 | A9* | 10/2017 | Ban | A61B 5/11 |

OTHER PUBLICATIONS

Dipietro L. et al., "A Survey of Glove-Based Systems and Their Applications," IEEE Transactions on Systems, Man, and Cybernetics—Part C: Applications and Reviews, vol. 38, No. 4, Jul. 2008.*

Kim, J-H. et al., 3-D Hand Motion Tracking and Gesture Recognition Using a Data Glove, IEEE International Symposium on Industrial Electronics (ISIE 2009), Seoul Olympic Parktel, Seoul, Korea, Jul. 5-8, 2009.*

King, R. C. et al., "Development of a Wireless Sensor Glove for Surgical Skills Assessment," IEEE Transactions on Information Technology in Biomedicine, vol. 13, No. 5, Sep. 2009.*

Simone, L. K. et al., "A low cost instrumented glove for extended monitoring and functional hand assessment," Journal of Neuroscience Methods 160 (2007) 335-348.*

Sturman, D.J. et al., "A Survey of Glove-based Input," IEEE Computer Graphics & Applications (1994) 33-39.*

Ziegler, J. et al., "Advanced Interaction Metaphors for RFID-Tagged Physical Artefacts," 2011 IEEE International Conference on RFID-Technologies and Applications, 73-80.*

* cited by examiner

Fig. 14a
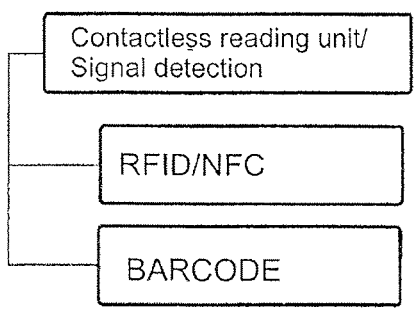
Fig. 14b
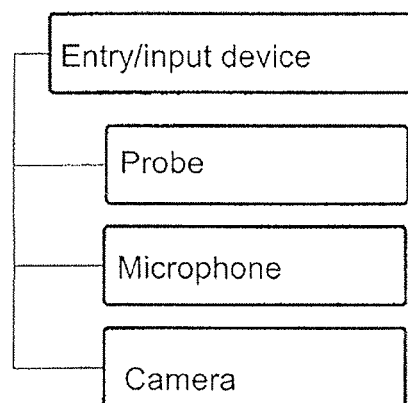
Fig. 14c

WORKWEAR UNIT HAVING A GLOVE THAT FASTENS A CONTROL SYSTEM AND FUNCTIONAL MODULE TO A USER'S BODY

RELATED APPLICATION

This application claims priority to DE Application 10 2014 015 082.8, filed Oct. 11, 2014, and DE Application 10 2015 111 506.9, filed Jul. 15, 2015.

TECHNICAL FIELD

The invention relates to a workwear unit for detecting, documenting, analyzing, monitoring and/or teaching processes, and further relates to a bracelet, a connecting piece, a glove, and a sensor module. The invention furthermore relates to a method of detecting, documenting, analyzing, monitoring, and/or teaching processes.

BACKGROUND

In modern working environments, such as production plants, any specialists brought in are increasingly assisted by control systems. The control systems help to minimize errors in assembling by indicating errors and recognizing the omission of assembling steps. The component build in, for example, must at first always be made known to the control system before mounting. This is usually carried out by sensor modules, using barcode readers, radio-frequency identification (RFID) readers or similar, for example. The control system can thus ensure that the correct component was installed.

These readers or reading units of the control systems are usually configured as hand-held devices such that the specialist must take the reading device in the hand for the detection of the component. A new processing step is thus created (take the reading unit into the hand, scan the component, put the reading unit aside) which improves the process quality but takes some time.

The object of the invention is to provide a system and a method of assisting the specialist, which reduces the time needed for data acquisition.

SUMMARY

The object is achieved by a workwear unit for detecting, documenting, analyzing, monitoring, and/or teaching processes. The unit includes a portable control system and at least one functional module connected with the control system, which has at least a sensor module and/or a peripheral device. The unit further includes at least a glove and/or a bracelet which can be worn on the hand or on the arm and which fastens the control system and/or the functional module to a user's body. The control system is, for example, integrated into the bracelet.

Within the meaning of the invention, portable is to be understood as "adapted to be put on", i.e. which can be worn on the body like an article of clothing or a piece of jewelry without having to grasp it. The workwear unit thus constitutes a so-called "wearable." Due to the fact that the workwear unit can be worn on the body, the user of the system, i.e. the specialist, has both hands free to carry out works. It is furthermore not necessary to laboriously seize an apparatus such as reading unit with the hand to be able to use the workwear unit, to scan components, for example. The time expenditure for the use of a system for assistance is thus reduced.

Here, a process means the sequence of manual activities carried out successively as is the case, for example, in the assembling of products. The control system controls the functional module and/or receives information from the functional module and determines the activity of the user of the workwear unit on the basis thereof. Furthermore, the glove may be a disposable item such that the workwear unit is also suited for activities having a high wear of the glove or in which a frequent change of the glove is necessary.

The peripheral device may comprise a release, a contact sensor, a bend sensor, and/or an antenna but may also have further peripheral devices known to computers.

The functional module preferably comprises a sensor module which has a barcode scanner, a RFID reader, a RFID writer, a near field communication (NFC) reader, a lacquer coating thickness measuring device, a motion sensor system, and/or an environment sensor system. Using the reading units such as the barcode scanner, the RFID reader and the NFC reader, it is possible to identify the components or objects to be installed. The motion sensor system and the environment sensor system however permit an extensive documentation of the operating sequence and the determination of the activity of the user that is performed.

The motion sensor system may, for example, have an accelerometer, a gyrometer, a magnetometer, and/or a nine-dimensional sensor. The environment sensor system comprises, for example, a temperature sensor, a moisture sensor, a light sensor, a microphone for recording the noise pollution, a radiation detector, a telemeter, a lamp, an air-pressure sensor, and/or an air quality meter for measuring pollutants, gases ($CO_2$), or the pollution by particles/dust.

The bracelet has for example a motion sensor system, an environment sensor system and/or a vitality sensor system, as a result of which an exact determination of the activities of the user, of the working environment and/or of his/her state of health is possible. The vitality sensor system comprises, for example, a pulsimeter, sensors for determining the oxygen content of the blood, an EMG sensor, a body temperature sensor, and/or sensors for determining the electrodermal activity.

In one embodiment of the invention, the bracelet has a socket for a plug, with the socket resting on the dorsal side on the wrist with respect to the state of the bracelet in which it is placed on the wrist. In one further example, the socket is rotationally symmetrical through 180°. The socket is thus approximately located at that point on the wrist, which would usually be taken up by the face of a watch. The socket can extend conically towards the wrist. It is in this way possible to connect the functional module with the bracelet in a simple and reliable manner.

The bracelet has, for example, an output which is arranged on the radial and dorsal side on the wrist with respect to a state of the bracelet in which it is placed on the wrist. Due to the fact that in contrast to the face of a watch, the output is shifted to the arm inner side, the output is also readable when works are carried out with the hands, for example the assembling of components, as a result of which a view on the output is possible at any time and without a large movement of the hand. The output is, for example, a display, LEDs, a LED matrix, a sound output, and/or a vibratory motor.

In a further embodiment of the invention, the bracelet and the functional module may be electrically connected with each other by a connecting piece, the connecting piece being firmly connected with the functional module and being detachably connected with the bracelet via a plug, or the connecting piece being firmly connected with the bracelet and being detachably connected with the functional module via a plug. Here, firmly connected within the meaning of the invention means permanently connected or connected so as to be detachable with a higher effort than the plug. The plug furthermore has contact pins, and the bracelet or the functional module has bushings for the contact pins, or vice versa. It is thus possible to configure the functional module independently of the bracelet and thus of the control system as a result of which the flexibility of the workwear unit is increased. This is particularly advantageous in case of a functional module connected with the glove.

The bracelet or the functional module, on the one hand, and the plug on the other hand, preferably have a plurality of contacts which are arranged in a contact pattern. The electrical connection between the bracelet or the functional module, on the one hand, and the plug on the other hand, being established by the contacts and the contact pattern being rotationally symmetrical through 180°. The rotational symmetry permits that the bracelet can be worn both on the left and on the right hand without having to make modifications to the hardware.

For example, the contacts are arranged in a 3×3 matrix, and a high frequency contact for a high frequency signal and at least four grounded contacts are provided, the contacts being grounded contacts which are directly adjacent to the high frequency signal, as a result of which a possibility of transmitting high frequency signals is created in a simple manner.

The plug, and/or the bracelet or the functional module, have, for example, magnets which fasten the connecting piece to the bracelet or to the functional module, which ensures a very simple and comfortable kind of a closing mechanism. In support thereof, it is also possible to provide magnetic material on the counterpart of the plug, i.e. on the bracelet or on the plug.

In one embodiment of the invention, the connecting piece has a bridge portion made of an elastic material which adjoins the plug and which is configured in an undulated manner, as a result of which it is possible to realize a flexible bridge portion in a simple manner. A cable establishing the electrical connection between the plug and the functional module or the bracelet may be integrated in the bridge portion or extend along the bridge portion. It is unimportant here whether the cable follows the undulated shape of the bridge portion.

The bridge portion is preferably configured such that the plug is prestressed against a plug-in direction as a result of which it is avoided that a loop is formed when the hand is flexed and by which the user can get tangled in projecting objects. This improves the occupational safety.

In a further variant embodiment of the invention, the peripheral device is integrated into the glove and/or the glove has a seat for the sensor module and/or the control system. The glove may also be configured as a partial glove or as an overglove. It is thus possible to make functions of a usual hand-held reading device available to the user without the user having to take a reading unit into the hand therefor.

The peripheral device preferably has a contact point via which an electrical connection with the control system is possible, as a result of which a central connecting point is produced. The contact point may also be configured as a wireless transmission unit such as a wireless area local network (WLAN) or Bluetooth module.

The peripheral device constitutes a functional module, for example, the connecting piece being fastened or the socket being provided at the contact point such that the advantageous connection by the connecting piece is permitted.

In a variant embodiment, the peripheral device has an electrical release which is in particular arranged outside on the index finger of the glove, particularly preferably in the region of the first phalanx of the finger. The release is, for example, a pushbutton or a slide control. A simply obtainable release as an input device for the workwear unit is thus realized.

The peripheral device has, for example, at least one contact sensor which is in particular located on a fingertip of the glove and is, for example, a pressure sensor or a capacitive touch sensor. It is thus possible that the workwear detects whether the user grasps an object. By the contact of two fingers, specific functions of the workwear unit may furthermore be triggered or be interpreted as pushing of a switch.

In one embodiment of the invention, the peripheral device has an antenna which is in particular arranged on the palm of the hand. The antenna may be a RFID antenna. The arrangement of the antenna on the palm of the hand permits a very reliable and unambiguous detection of objects grasped by the user.

The peripheral device has, for example, a bend sensor which is arranged on a finger of the glove. The bend sensor may be arranged laterally on the finger, in particular along the neutral line, the neutral line relating here to a flexing of the finger. Due to the bend sensor it is possible to detect specific operations of the user, such as the release of an electrical screw driver.

The bend sensor is, for example, arranged on the side of the back of the hand of a finger of the glove and extends over a joint of the finger, the bend sensor being firmly connected with the glove merely at its end facing the wrist, which improves the wearing comfort of the glove since no pressure points occur at the joint due to a rigid and stiff bend sensor.

In a further embodiment of the invention, the glove has conducting tracks which electrically connect the contact point with the remaining peripheral devices such that the signal of all components may be tapped at the contact point.

The conducting tracks, the contact point, the antenna, the contact sensor, and/or further components are, for example, made of conductive yarn, wire or strands which are sewed or woven into the glove, or which are enclosed by weaving which permits the safe and protected integration of the conductive tracks into the glove.

The conducting tracks, the contact point, the antenna, contacts of the release, the contact sensor, the bend sensor, and/or further components may be printed on a foil which is integrated into the glove. The printing may be carried out using conductive ink having silver particles, or in case of the bend sensor also using a resistive ink. In this case, the glove is configured so as to have a double layer on the hand inner side and/or on the back of the hand, the foil being arranged between the two layers. A connection of the layers is performed by bonding or sewing. In this way, the peripheral device can be realized and integrated into the glove in a very cost-effective manner.

In a further variant embodiment of the invention, the seat is a pocket into which the sensor module and/or the control system may be plugged and out of which the sensor module and/or the control system may be pulled out again. Or, the seat is a guide, in which the sensor module and/or the control system may be shifted in and out, as a result of which the glove may be used with different sensor modules and/or with the control system. The guide or the pocket may be arranged on the back of the hand of the glove or on a finger of the glove so as to impede the user as little as possible during its work. The plugging-in or insertion and the withdrawal are preferably performed without any tool and in a non-destructive manner. In one further example, the seat comprises a dovetail guide.

The pocket or the guide is preferably partly open such that a connecting portion of the sensor module can be plugged into the pocket or can be inserted into the guide.

The guide has, for example, two rails which delimit the guide in its transverse direction such that the sensor module can be simply inserted into the guide.

At one end of the guide, the rails may be connected with each other by a termination, the termination delimiting the guide in its longitudinal direction as a result of which the sensor module is prevented from unintentionally slipping out of the guide. The end of the guide having the termination is, for example, the end of the guide facing the wrist.

The guide preferably has a base plate which is fastened to the glove and from which the termination and/or the rails extend in particular at an acute angle towards each other. The base plate may be fastened to the glove by vulcanizing, bonding, or sewing. A firm and stable configuration of the guide is in this way possible.

In one embodiment of the invention, at least one peripheral contact forming the contact point is provided on the pocket or on the guide, in particular on the base plate such that no further components are to be applied onto the glove for the contact point.

A sensor contact which is electrically connected with the peripheral contact is preferably provided on the pocket or on the guide, the sensor contact being adapted to be connected with a continuous contact on the sensor module, which permits a detachable electrical connection between the peripheral device and the sensor module. In one further example, the sensor contact is provided on the termination of the pocket or guide.

In a further embodiment of the invention, the sensor module and/or the control system can be fastened to the glove the seat. The sensor module or the control system can then comprise a connecting portion that can be introduced into the pocket or can be inserted into the guide. A simply operable and reliable kind of fastening of the sensor module or of the control system to the glove is thus realized. The connecting portion may be configured to have a trapezoidal or dovetail cross-section.

In a further variant embodiment of the invention, the sensor module is the functional module, it is thus possible to realize a workwear unit that is simple because it is made of few components.

In one embodiment of the invention, the sensor module and the peripheral device constitute the functional module, the sensor module having a continuous contact which may be electrically connected with the control system via the connecting piece. The continuous contact contacts the sensor contact of the pocket or that of the guide when the sensor module is inserted into the pocket or in the guide. A connection of the contact point and thus of the peripheral device with the control system is therefore permitted.

The sensor module may have an output or indicator. For example, the output device or indicator can be a display, LEDs, or a LED matrix as a result of which the user can receive information from the sensor module.

The object is further achieved by a bracelet for a workwear unit according to the claims, wherein merely those features of the claims mentioned have to be taken into account which describe the bracelet.

The object is further achieved by a connecting piece for a workwear unit according to any of claims 7 to 10, wherein only those features of the claims mentioned have to be taken into account which describe the connecting piece.

The object is further achieved by a glove for a workwear unit according to the claims. The glove has, in particular, a firmly applied pocket or guide for the detachable insertion of the sensor module and/or of the control system, wherein merely those features of the claims mentioned which describe the glove have to be taken into account.

The object is further achieved by a sensor module for a workwear unit according to the claims, wherein merely those features of the claims mentioned which describe the sensor module have to be taken into account.

The object is further achieved by a method of detecting, documenting, analyzing, monitoring and/or teaching processes which comprises manual activities, the method comprising the following steps:
a) acquiring information of the sensor module and/or of the peripheral device of the workwear unit according to the claims, and
b) determining the activity of the user of the workwear unit on the basis of the acquired information.

The activity of the user is, for example, a motion, a sequence of motions, the grasping of a tool or the actuation of a tool. Motions and sequences of motions of the user may be determined by the motion sensor system of the workwear unit. The grasping of a tool may be defined by the detection of a RFID tag, a NFC tag, or by reading a barcode provided on or in the tool. The time at which the tool is grasped or actuated can be determined by the bend sensors. The motion sensor system can also recognize the actuation of a tool.

Due to the fact that the activities of the user are determined by the workwear unit, a correction of errors and thus an assistance of the user is possible without further time-expensive processing steps being necessary.

The motion sensor system of the workwear unit, in particular when it serves to the determination of position, is calibrated in that at least one preferably stationary anchor point defined in the working environment is passed and the spatial position of the workwear unit is thus determined. The anchor point may be a RFID tag, a NFC tag, the grasping of a tool out of a support, the release of a machine, or the scanning of a barcode. An exact spatial determination of the workwear unit and thus of the user in the space is therefore precisely possible by the motion sensor system. Though the motion sensor system permits to retrace relative motions over a short period of time, it has a drift such that the absolute position in space can no longer be determined precisely after some time. By passing the anchor points, the absolute position of the workwear unit becomes known again and thus the drift of the motion sensor system again compensated.

In one configuration of the invention, the position and/or the motion of the user or of his/her hand may be determined by triangulation with respect to several anchor points. In this case, RFID or NFC techniques are preferably applied. Due to the determination of the position of the user in the space, it is possible to determine the kind of activity and the process more precisely.

The specific activity of the user can, for example, be used for controlling a machine which permits a simpler and faster operation of machines.

In one variant embodiment of the invention, the plausibility of the user's activity is checked and a signal is output to the user on the basis of the result of the check, errors being thus directly pointed out to the user. This in turn improves the speed and quality of work of the process.

The activity is preferably stored in a memory along with information about the error rate obtained by the plausibility check, the work time, the information of the vitality sensor system and/or the information of the environment sensor system. This information may be analyzed later to thus optimize the performed process. In this way, the method also serves to increase the productivity.

The use of the workwear unit and the method are of course not limited to the assembling of products but can be transferred to all fields in which manual activities are carried out. An application of the workwear unit and of the method in logistics is for example conceivable.

These and other features may be best understood from the following drawings and specification.

BRIEF DESCRIPTION OF THE DRAWINGS

Further features and advantages of the invention will become apparent from the description below and from the accompanying drawings to which reference is made. The figures show:

FIG. 14a shows an example selection of different possible sensors of the sensor module, FIG. 14b shows an example selection of different entry and input devices of the workwear unit, FIG. 14c shows possible components of a nine-dimensional sensor.

DETAILED DESCRIPTION

Figure 1:
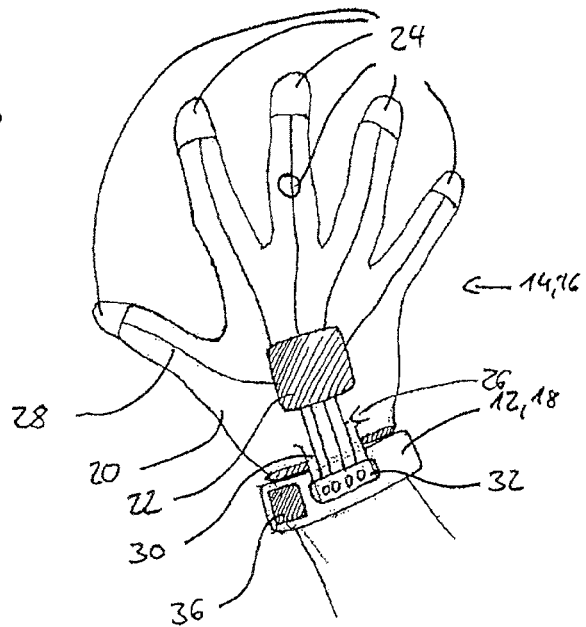
FIG. 1 shows a workwear unit according to the invention in a top view in a state in which it is worn.

FIG. 1 shows a workwear unit 10 in a worn condition, i.e. in a state in which it is fastened to the hand or the arm of a user.

The workwear unit 10 has a control system 12 and a functional module 14 which comprises several peripheral devices 16 in the embodiment shown.

In the embodiment shown, the workwear unit 10 has a bracelet 18 into which the control system 12 is integrated, and a glove 20 into which the peripheral devices 16 are integrated.

The control system 12 has a micro-computer which comprises a power supply, a timer, and a memory. The control system 12 may furthermore be connected with an external computer and/or the functional module 14 via a radio signal, for example via WLAN or Bluetooth.

The glove 20 may be configured as a disposable glove or as an expendable item.

Both the bracelet 18 and the glove 20 serve to fasten the control system 12 and the functional module 14 in the form of the peripheral devices 16 to the user's body.

The workwear unit 10 is thus adapted to be worn on the arm or on the hand like an ordinary bracelet or an ordinary glove.

Figure 2:
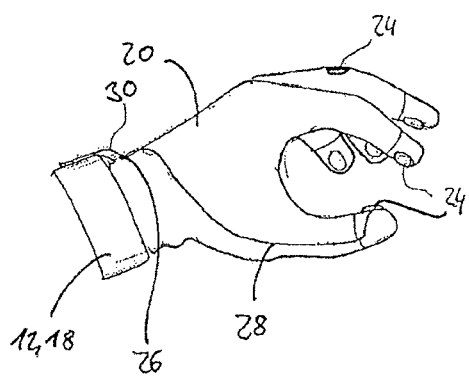
FIG. 2 shows the workwear unit according to FIG. 1 in a lateral view.

In the first embodiment shown in FIG. 1 and FIG. 2, the functional module 14 has a RFID reader 22 and contact sensors 24 as peripheral devices 16.

The RFID reader 22 is fastened to the glove 20 at the back of the hand, i.e. on the dorsal side.

The contact sensors 24 are respectively arranged on a fingertip of the glove 20 and can also be fastened on the upper side of one or more fingers.

The contact sensors 24 are, for example, pressure sensors, capacitive touch sensors, or inductive or magnetic elements.

The peripheral devices 16 furthermore have a contact point 26 on the glove 20 to which the remaining peripheral devices 16, in this case the RFID reader 22 or RFID writer, and the contact sensors 24 are connected by conducting tracks 28.

The contact point 26 may also be configured as a wireless transmission unit such as a WLAN or Bluetooth unit.

A connecting piece 30 is firmly connected with the glove 20 in the region of the contact point 26. The other end of the connecting piece 30 which is not connected with the glove 20 has a plug 32 by which the connecting piece may be inserted into the bracelet 18.

Figure 3A:
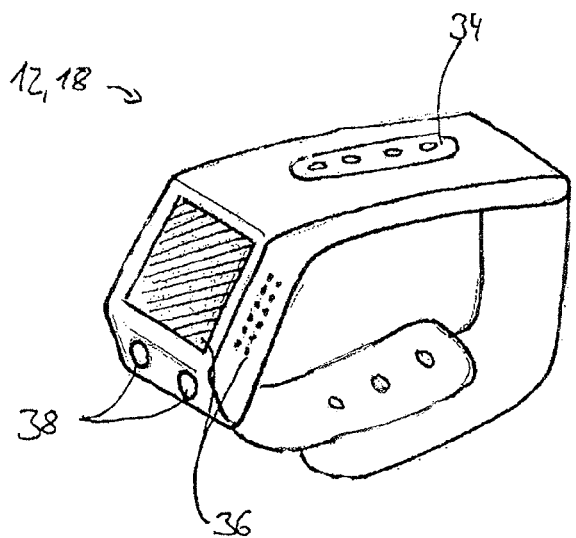
FIGS. 3a and 3b show a control system of the workwear unit of FIG. 1 which is configured as a bracelet in two different perspective views and in an unworn state.
Figure 3B:
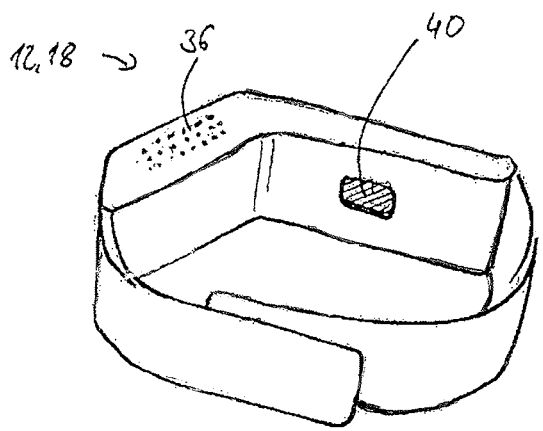

FIGS. 3a and 3b show the bracelet 18 in detail without the user's arm.

On its upper side, i.e. the side resting dorsally on the wrist in a condition worn on the arm, the bracelet 18 comprises a socket 34 into which the plug 32 can be plugged in. In other terms, the plug 32 is located at that point of the bracelet 18 at which the face of a watch is arranged.

Owing to the plug 32, an electrical connection between the functional module 14, here the peripheral devices 16, and the control system 12 is realized by the connecting piece 30 and the contact point 26.

The plug 32 is adapted to be detached from the bracelet 18, i.e. to be separated from the bracelet 18 without high effort, without any tool, and in a non-destructive manner.

The connecting piece 30 cannot be separated from the glove 20 or merely with higher forces and more concentration than the plug 32 is separated from the bracelet 18.

It is of course also conceivable that the plug 32 is configured on the glove 20 and that the connecting piece 30 is configured to be firmly connected with the bracelet 18.

The bracelet 18 further has an output 36 which is arranged on the radial and on the dorsal side on the wrist with respect to a condition worn on the arm. In other words, the output 36 is arranged on the wrist as seen from the plug 32 in the direction of the thumb and is bent with respect to the plug 32.

The output 36 may be a display, LEDs, a LED array, a loudspeaker for the output of sound and/or a vibratory motor. In the embodiment shown, the output 36 is a display.

On the side of the output 36 facing away from the socket 34, two operating buttons 38 are provided on the bracelet which directly adjoin the output 36 and which are preferably located below the display and therefore at the transition of the lower side of the wrist and the inner side face of the wrist. This position simplifies a fast actuation of the operating buttons 38.

A microphone or the microphone of the environment sensor system and a camera are conceivable as additional input devices.

Gestures can be sensed via a camera or other sensors such that the workwear unit can react to a gesture control.

The bracelet 18 may further comprise a motion sensor system (not shown) which includes, for example, an accelerometer, a gyrometer, a magnetometer, a signal acquisition unit of different frequencies, or a 9-dimensional sensor comprising these components.

As can be seen in FIG. 3b, a vitality sensor system 40 is provided in the bracelet 18 on the side of the bracelet 18 facing the arm, for example in the region of the plug 32.

The vitality sensor system 40 comprises, for example, a pulsimeter, sensors for determining the content of oxygen in the blood, EMG sensors, body temperature sensors, and/or sensors for determining the electrodermal activity.

Figure 4:
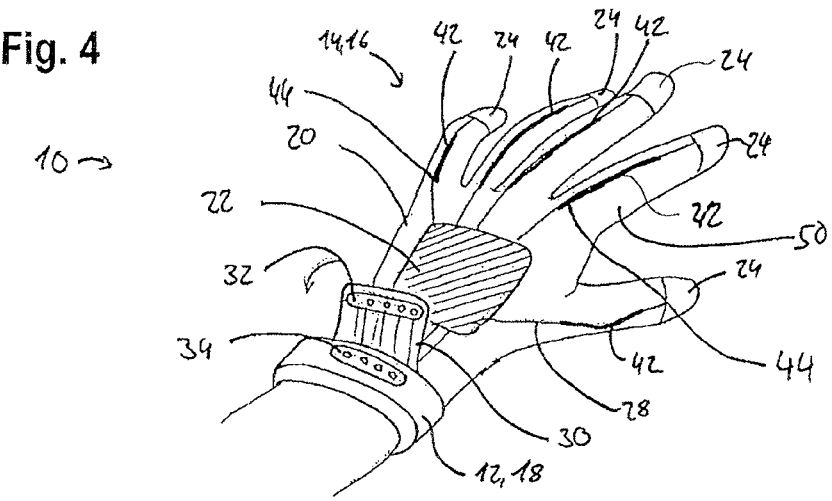
FIG. 4 shows a second embodiment of a workwear unit according to the invention.

FIG. 4 shows a second embodiment of the workwear unit 10. This embodiment and all further embodiments substantially correspond to the first embodiment according to FIGS. 1, 2, 3a and 3b such that only the differences are explained below. Identical parts or parts having the same function are provided with the same reference numbers.

In the second embodiment according to FIG. 4, the bracelet 18 is configured without a display.

However, the glove 2 comprises in addition to the RFID reader 22 or the RFID writer and the contact sensors 24 further peripheral devices 16 in the form of bend sensors 42. In the embodiment shown, the bend sensors are arranged on the fingers of the glove 20 on the back side of the hand and extend over at least one joint of the user's finger.

The bend sensors 42 are, for example, arranged in a guide (not shown) on the glove 20 and are firmly connected with the glove 20 only at their end 44 facing the user's wrist. In this way, the bend sensor 42 can move within the guide relatively to the glove 20 when the user flexes the individual fingers.

It is however also conceivable that the bend sensors 42 are located laterally on the finger, for example along the neutral line which is defined with respect to the flexing of the corresponding finger.

Figure 5:
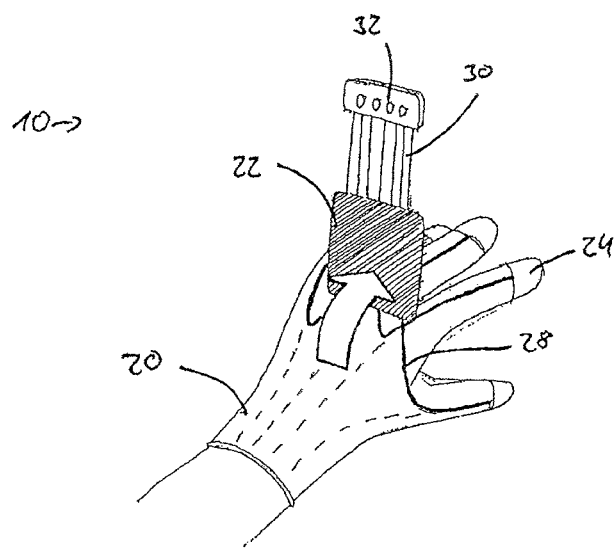
FIG. 5 shows a glove according to a third embodiment of a workwear unit according to the invention in the worn state.

FIG. 5 provides a third embodiment of the workwear unit 10. However, only the glove 20 is shown which is configured such that the peripheral devices 16 may be detached from the glove 20. The peripheral devices 16 can then be applied again onto a new glove 20. In this embodiment, the glove 20 is thus a cost-effective disposable or throw-away article which is temporarily equipped with the peripheral devices 16 which are to be used further.

Figure 6A:
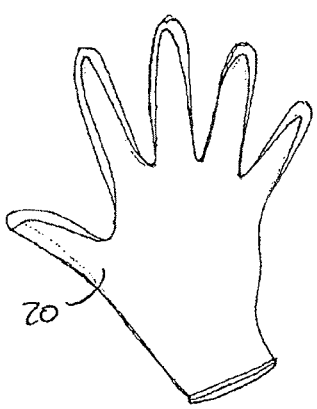
FIG. 6a shows an embodiment of the glove of the workwear unit according to the invention.
Figure 6B:
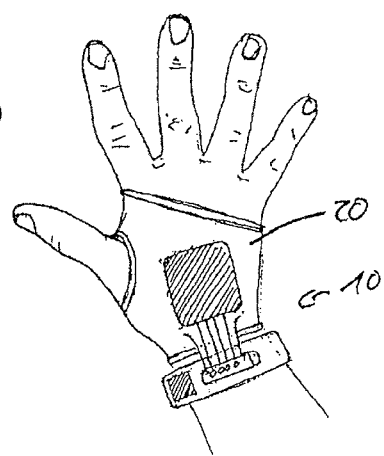
FIG. 6b shows an embodiment of the glove of the workwear unit according to the invention.

FIGS. 6a and 6b show further embodiments of the glove 20, wherein the glove can also be configured only as a partial glove or as an overglove like in FIG. 6b. This is particularly useful if the user wishes to perform fine motor operations requiring a fine feeling.

Figure 7:
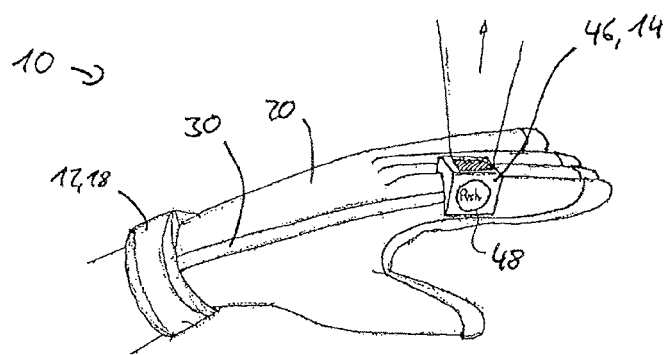
FIG. 7 shows a fourth embodiment of a workwear unit according to the invention.

FIG. 7 shows a fourth embodiment of the workwear unit 10.

In this fourth embodiment, the workwear unit 10 has a sensor module 46 which simultaneously constitutes the functional module 14. The sensor module 46 is again connected with the bracelet 18 via a connecting piece 30, the connection between the bracelet 18 and the sensor module 46 being not detachable in the embodiment shows. This may however be configured in a detachable manner without difficulty, as is for example, shown above and below.

In this fourth embodiment, the bracelet 18 has no output.

In this fourth embodiment, the sensor module 46 is a barcode scanner arranged on the forefinger of the glove 20. A fastening to the back of the hand is also conceivable.

However, it is also conceivable that the sensor module 46 has a RFID reader, a RFID writer, a NFC reader, a motion sensor system, an environment sensor system, and/or a lacquer coating thickness measuring device.

The environment sensor system serves to detect the work environment and comprises, for example, a temperature sensor, a moisture sensor, a light sensor, a microphone, a radiation detector, a lacquer coating thickness measuring device, a telemeter, a lamp, an air pressure sensor, and/or an air quality meter for measuring pollutants, gases ($CO_2$), or particles or the pollution by dust. The microphone may also be used for the entry of voice instructions.

The barcode scanner further comprises an electrical release 48 which is arranged outside on the forefinger in the region of the first phalanx of the finger 50. The electrical release 48 may also be configured as peripheral device 16, for example as a pushbutton or a slide control separate from the bend sensor 42.

Figure 8:
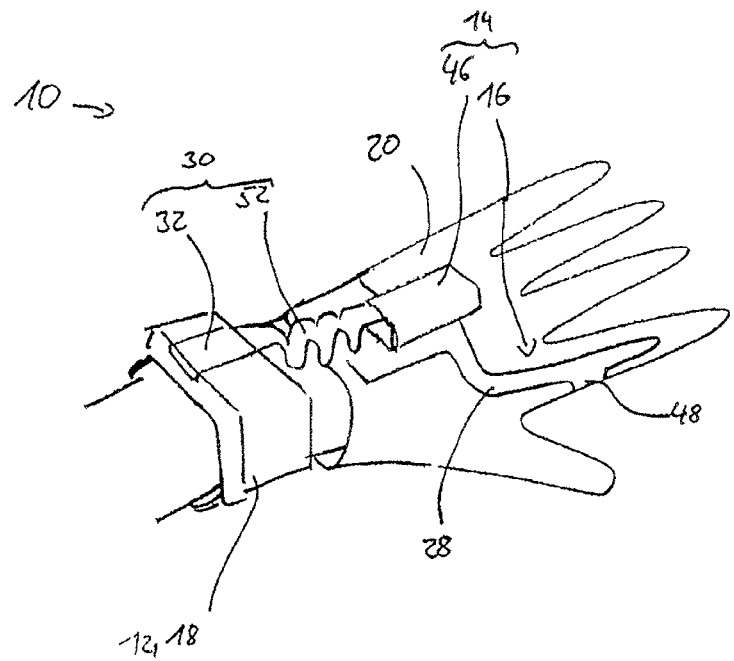
FIG. 8 shows a fifth embodiment of a workwear unit according to the invention.

FIG. 8 shows a fifth embodiment of the workwear unit 10. In this embodiment, the workwear unit 10 comprises a control system 12, a sensor module 46, and further peripheral devices 16. The sensor module 46 and the peripheral devices 16 constitute together the functional module 14.

In this fifth embodiment, the connecting piece 30 is firmly connected with the sensor module 46. The connecting piece 30 comprises between the plug 32 and the sensor module 46 a bridge portion 52 adjacent to the plug 32.

The bridge portion 52 is made of an elastic material and is, for example, injection-molded and configured in an undulated manner. In the embodiment shown, the cable forming the electrical contact between the plug 32 and the sensor module 46, i.e. the functional module 14, is integrated, for example molded into the bridge portion 52. It is also conceivable that the cable extends outside the bridge portion 52 along the latter, irrespective of whether the cable follows the undulated shape of the bridge portion 52 or not.

Figure 9A:
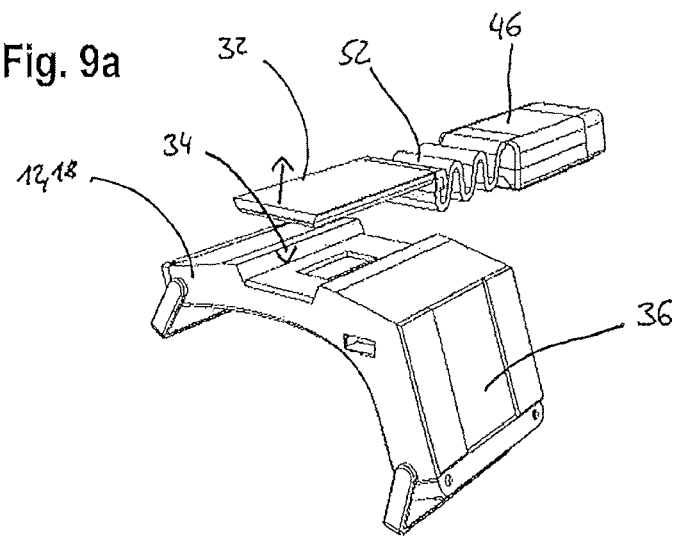
FIG. 9a shows a bracelet, a connecting piece and a sensor module of the workwear unit of FIG. 8.
Figure 9B:
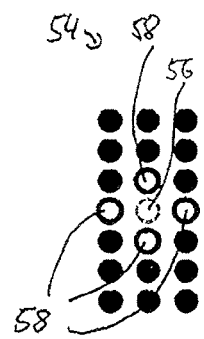
FIG. 9b shows the contact pattern of the workwear unit according to FIGS. 8 and 9a, FIGS. 10a and 10b show the glove of the workwear unit according to FIG. 8 in a dorsal and palmar view, respectively.

The plug 32 is electrically connected with the bracelet 18 via contacts arranged in a contact pattern 54. An example contact pattern is shown in FIG. 9b.

The contacts are arranged in the socket 34 of the bracelet 18 which in this embodiment runs conically towards the wrist. This means that the contacts are arranged in a deepened manner towards the wrist.

The socket 34 is configured as a recess in the bracelet 18 which extends parallel to the longitudinal axis of the user's arm and which is open to both sides of the bracelet 18.

The socket 34 is configured so as to be rotationally symmetrical through 180° such that the plug 32, and thus the connecting piece 30, are adapted to be arranged on both sides of the bracelet 18 and connected with the bracelet 18. In this way it is achieved that the bracelet 18 can be worn both on the left and on the right wrist, the functional module 14 being in both cases adapted to be arranged on the hand-side face of the bracelet 18.

A bracelet-side projection may also serve as a socket, the plug 32 having a complementary recess to be placed onto the projection.

The contacts are realized by contact pins (not shown) on the plug 32 and by bushings for the contact pins (not shown) on the bracelet 18. An inversion of the contact pins and the bushings is also possible.

The contact pattern 54 is also rotationally symmetrical through 180°, and the contacts are arranged in the socket 34 in accordance with the contact pattern 54 such that the plug 32 can be plugged-in from both sides also in this case.

The contact pattern 54 is at least a 3×3, here a 3×7 matrix. The central contact may also be configured as a high frequency contact 56 for a high frequency signal, the contacts 58 directly adjacent to the high frequency contact 56 being grounded and thus permitting a shielding of the high frequency contact 56.

For a simpler connection, the plug 32 and/or the bracelet 18 comprise magnets (not shown) which serve to fasten the connecting piece 30 to the bracelet 18. If only one of both parts, i.e. the plug 32 or the bracelet 18, is provided with magnets, the corresponding counterpart has a magnetic metal to permit the fastening by magnets.

The bridge portion 52 may furthermore be prestressed such that the plug 32 is prestressed against its direction of insertion. In the unplugged position (not shown), the plug 32 thus projects with respect to the sensor module in the direction of the arrow of FIG. 9a.

Figure 10A:
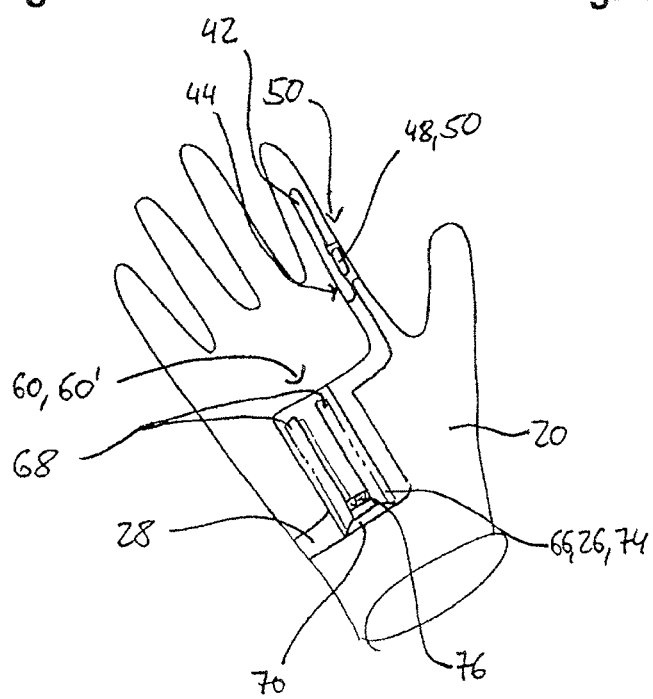
FIG. 10c shows a further embodiment of the glove of the workwear unit according to FIG. 8 in a dorsal view.
Figure 10C:
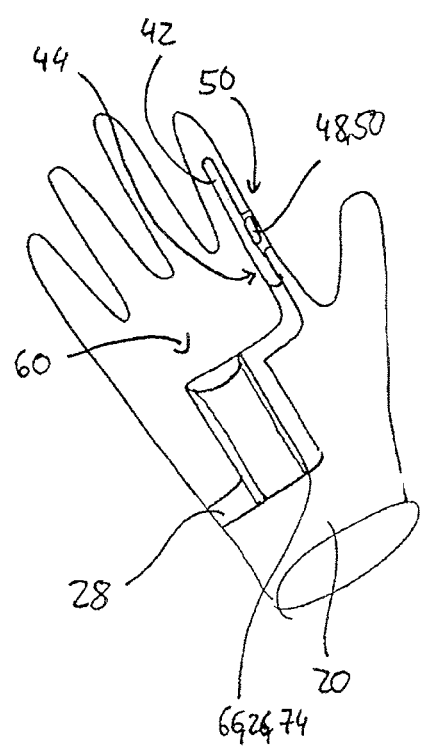
Figure 10B:
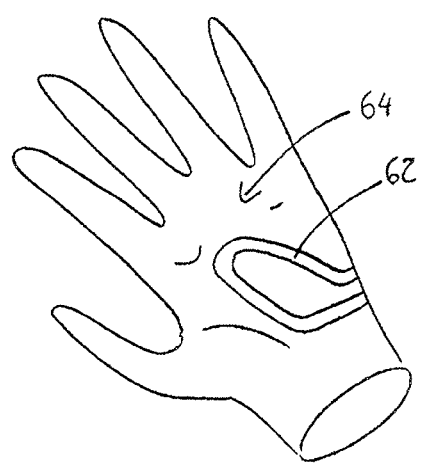

FIGS. 10a and 10b show the glove 20 of the fifth embodiment of the workwear unit 10 in a view onto the back side of the hand, i.e. in a dorsal view (FIG. 10a), and in a palmar view, i.e. in a view onto the palm of the hand (FIG. 10b). The glove 20 has a seat 60 for the sensor module 46.

Figure 11A:
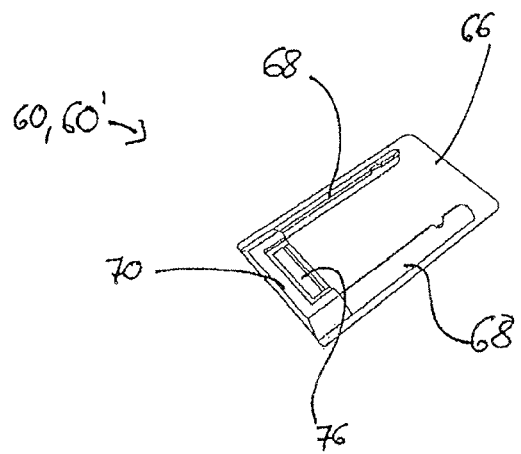
FIG. 11a shows the seat fastened onto the glove according to FIG. 10a, FIG. 11b the connection between the sensor module and the seat according to FIG. 11a, FIG. 12 shows an exemplary schematic plugging chart of a workwear unit according to the invention.
Figure 11B:
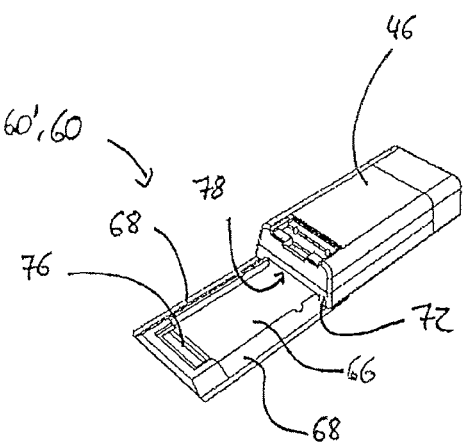
Figure 12:
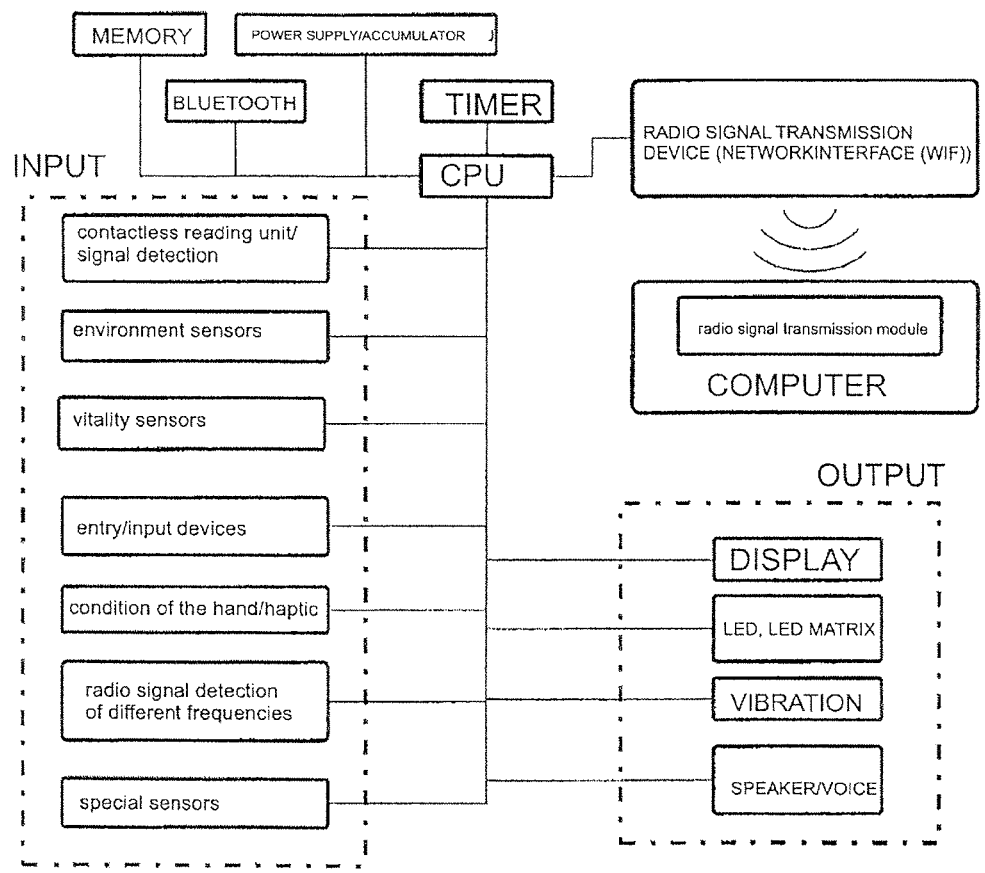
Figure 13A:
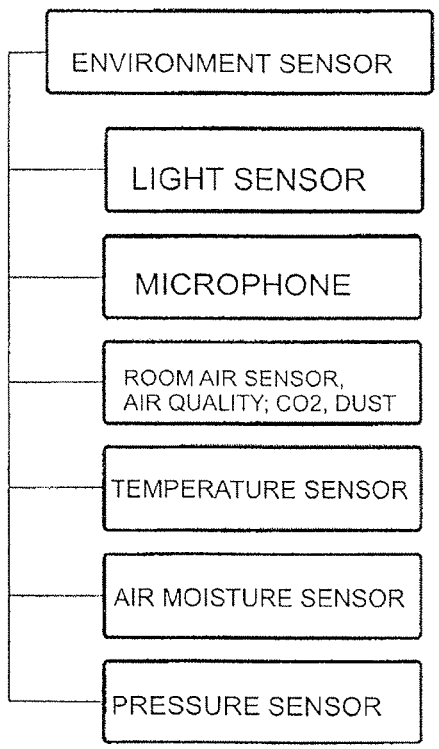
FIGS. 13a and 13b show an example selection of the possible sensors of the environment sensor system and the vitality sensor system, respectively.
Figure 13B:
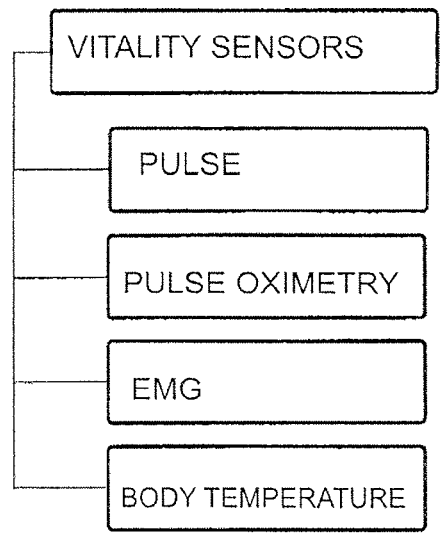
Figure 15:
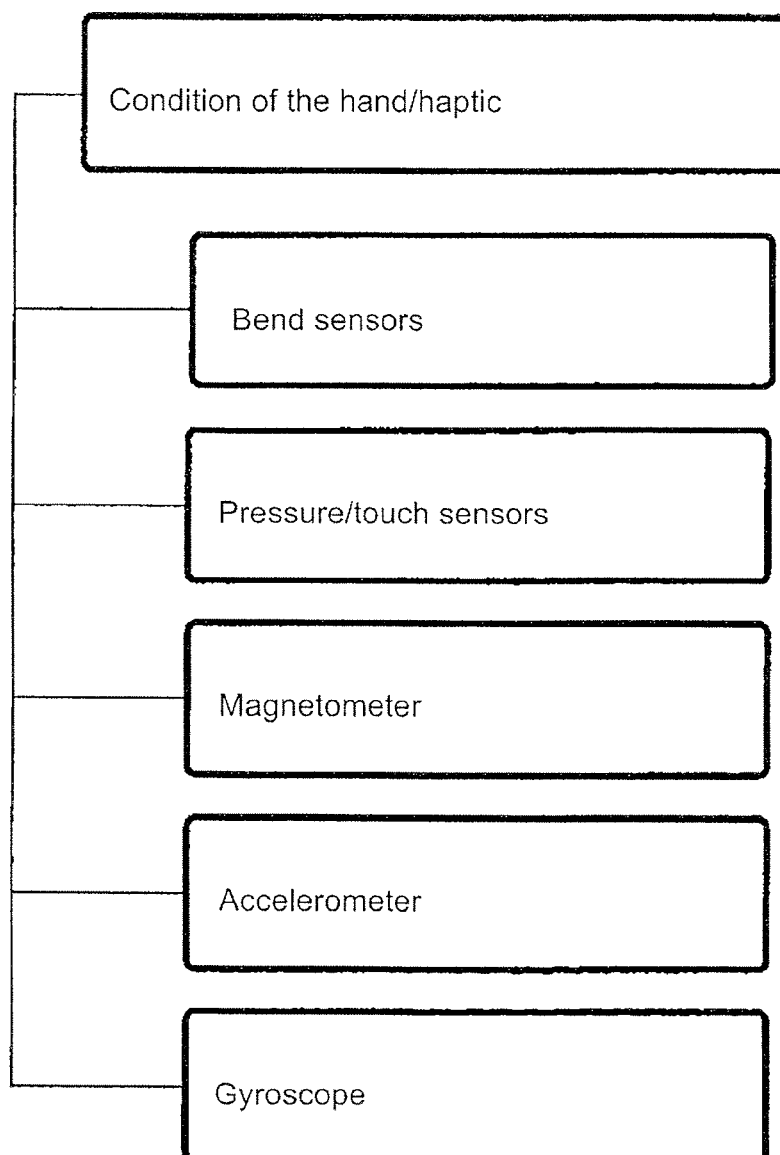
FIG. 15 shows an example selection of the components provided in/on the glove.

The seat 60 is, for example, configured as a guide 60' in which the sensor module 46 (and, if necessary the control system 12) can be shifted in and out (see FIG. 11b).

The seat 60 is located on the back of the hand of the glove 20.

FIG. 10c shows a variant of this embodiment in which the seat 60 is configured as a pocket into which the sensor module 46 (and if necessary the control system 12) can be plugged and out of which the sensor module 46 (and if necessary the control system 12) may be withdrawn again (see FIG. 11b).

The sensor module 46 (and if necessary the control system 12) can also be adapted to be only partly plugged into the pocket, merely a connecting portion 72 of the sensor module 46 being, for example, adapted to be plugged into the pocket.

In this embodiment of FIGS. 10a and 10c, the peripheral devices 16 are a bend sensor 42, an electrical release 48, and an antenna 62 which is, for example, a RFID antenna. As described with respect to the previous embodiments, the bend sensor 42 is arranged on a finger on the side of the back of the hand and the electrical release 48 on the first phalanx 50 of the forefinger of the glove 20.

The antenna 62 is provided on the palm 64 of the glove 20. It can be made of a simple conductor loop of conductive material.

The conducting tracks 28, the contact point 26 and the antenna 62 may be made of conducting yarn, wire or of strands sewed into the glove 20, or enclosed by weaving. This may also apply to further peripheral devices 16 not present in this embodiment.

It is also conceivable that the conducting tracks 28, the contact point 26, the antenna 62, contacts of the electrical release 48, and/or the bend sensor 42 are printed onto a foil (not shown). This may also apply to peripheral devices 16 which are not provided in this fifth embodiment.

These peripheral devices 16 can be printed onto a foil using a conductive ink. The ink may, for example, be provided with silver particles or be a resistive ink in the case of the bend sensor.

In case the peripheral devices 16 are printed onto the foil, the hand inner side and/or the back of the hand of the glove 20 is configured in two layers, the foil being then provided between the two layers. The connection of the two layers with each other is then realized by bonding or sewing. The peripheral devices 16 can in this way be integrated into the glove 20 in a very cost-effective manner.

In FIG. 11a, the seat 60, in this case the guide 60' is represented separately. The guide 60' is fastened to the glove 20 by vulcanization, bonding, or sewing.

The guide 60' has a base plate 66 from which two rails 68 extend.

The rails 68 can be bent with respect to the base plate 66 and extend at an acute angle towards each other.

The two rails 68 delimit the guide 60' in its transversal direction, in the shown embodiment of FIG. 10a thus transversely to the longitudinal axis of the user's arm. The rails 68 are connected with each other by a termination 70.

The termination 70 delimits the guide 60' in its longitudinal direction, i.e. parallel to the longitudinal axis of the user's arm in the embodiment shown in FIG. 10a.

The termination 70 is provided on the face of the guide 60' which is turned towards the wrist.

In this way, a guide 60' is obtained into which the sensor module 46 is adapted to be inserted from one direction, i.e. from the side of the guide 60' which is directed towards the fingertips. This is shown in FIG. 11b, the sensor module 46 being shown without the connecting piece 30 connected therewith.

To this end, the sensor module 46 has a connecting portion 72 which may be configured so as to have a trapezoidal or dovetail cross-section.

The angles of the trapezoidal or dovetail shape are chosen to correspond to the angle of the rails 68. The connecting portion 72 of the sensor module 46 can thus be inserted into the guide 60', as a result of which the sensor module can be fastened to the glove 20 as shown in FIG. 11b. The guide 60' thus forms a dovetail guide, for example.

In addition to the mechanical fastening of the sensor module 46, the seat 60, here explained by way of example with reference to the guide 60', also serves for the electrical contact between the peripheral devices 16 and the control system 12.

To this end, the base plate 66 has peripheral contacts 74 which are connected with the peripheral devices 16 by the conducting tracks 28. The base plate 66 thus forms the contact point 26 of the peripheral devices 16.

Sensor contacts 76 which are each separately connected with the peripheral contacts 74 are moreover provided on the guide 60', for example on the termination 70.

If the sensor module 46 is plugged or inserted into the seat 60, these sensor contacts 76 are connected with continuous contacts 78 of the sensor module 46. These continuous contacts 78 are in turn electrically connected with the connecting piece 30. An electrical connection between the control system 12 and the peripheral device 16 is in this way realized by the peripheral contacts 74, the sensor contacts 76, the continuous contacts 78, and finally the connecting piece 30.

The sensor module 46 may also have an indicator, a display, LEDs, or a LED matrix, for example.

Moreover, it is conceivable that the control system 12 is also adapted to be fastened to the glove 20. In this case, the control system 12 and the sensor module 46 form a structural unit which can be connected with the glove 20 as described with respect to the fifth embodiment.

Any combinations of the different sensor systems, arrangements and connecting possibilities of the different embodiments are of course conceivable. The embodiments shown therefore constitute only example combinations of sensors, connecting possibilities and fastening possibilities.

It is also conceivable that the connecting piece 30 is firmly connected with the bracelet 18 and is connected with the functional module 14 by the plug 32. To this end, the functional module 14 has an appropriate socket 34.

FIGS. 12 to 15 show the different kinds of sensors and the use thereof in a workwear unit 10.

During the use of the workwear unit 10, the control system 12 controls the functional module 14 and receives signals from the functional module 14 and determines therefrom the activity of the user of the workwear unit 10

To this end, the control system 12 first acquires the information of the sensor module 46 and/or of the peripheral devices 16. Using this information, the control system 12 can now determine the activity of the user. This information about the activity may then be used to detect, document, analyze, monitor, and/or teach processes which comprise a manual activity.

An application is conceivable in which the user has to mount a component of a product in a production line.

Using the motion sensor system of the workwear unit 10, it is then possible to determine the motions and the sequences of motions of the user. This is sufficient to unambiguously identify the screwing of a screw by the rotation of the user's hand, for example. Using the motion sensor system, it is furthermore also possible to unambiguously identify the insertion of fastening clips during which an abrupt motion occurs. The actuation of a tool can furthermore be identified using the bend sensors, the actuation of the trigger of an electrical screwdriver, for example.

A tracing, a so-called tracking of the motion of the user or of the hand of the user in the space merely on the basis of the motion sensor system is not possible as the motion sensor system drifts.

However, the motion sensor system can be regularly calibrated by passing anchor points. At the anchor points, the spatial position of the user or of the hand of the user is known. Anchor points are, for example, formed by RFID tags, NFC tags which are fixed in a stationary manner in the working environment of the user. When the user now passes such a RFID or NFC tag with the workwear unit 10, the control system 12 can derive the exact, absolute position of the user therefrom and thus again calibrate the motion sensor system. Possible anchor points are for example also the grasping of a tool out of a tool holder, the triggering of a machine by a button, or the scanning of a barcode.

The identification of tools grasped by the user can also be carried out by means of RFID- or NFC tags provided in or onto the tool. A tool may also be identified by scanning a barcode.

A further possibility for the determination of the position of the user or of the hand of the user is provided by triangulation, i.e. the distance measurement from the hand to different anchor points. The absolute position of the hand in the space may then be derived on the basis of the distances to the anchor points.

Due to the detection of the process activities, it is possible to document and to analyze processes. It is also possible to directly monitor the work of a user and to give a direct feedback about the success of his/her activities ("forcing of processes").

Figure 16:
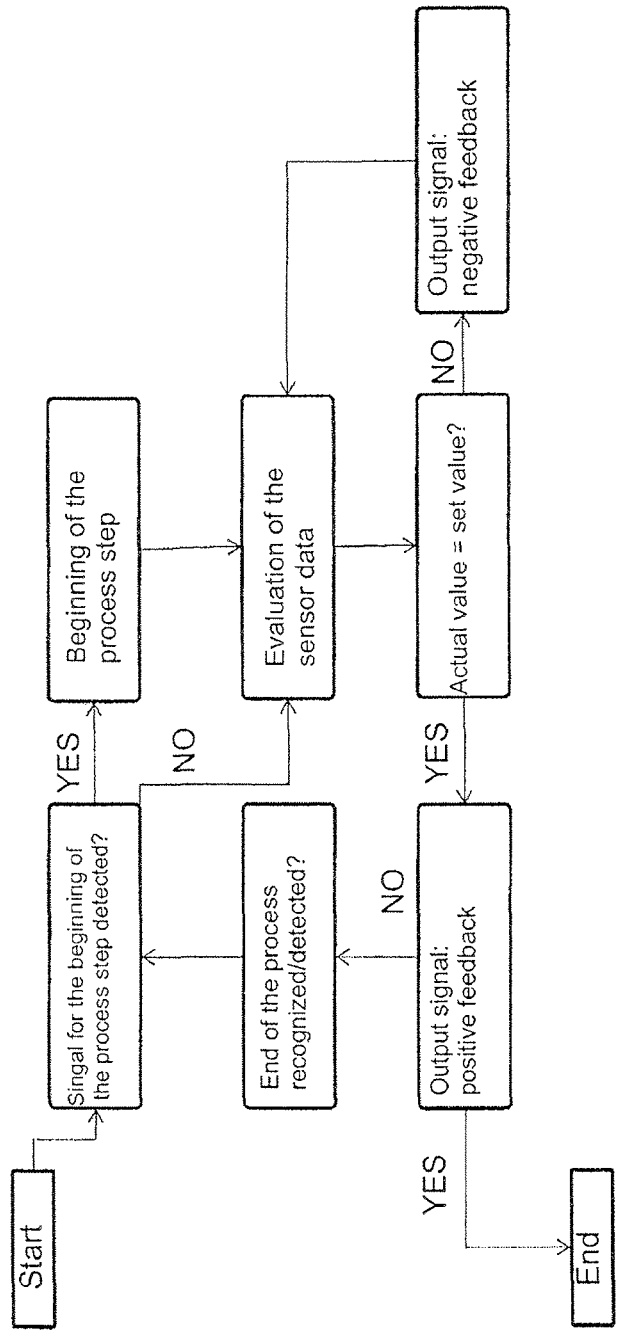
FIG. 16 shows a schematic illustration of a method of forcing process sequences and of the output of feedback to the user, respectively.

Such a method is schematically shown in FIG. 16. To this end, the beginning of a processing step is at first sensed. The beginning is for example signalized by the user himself/ herself, for example by activating the electrical release 48, or the workwear unit 10 senses the beginning automatically, for example by passing a determined anchor point.

After the beginning of the process, the determined information of the functional module 14 is evaluated, and on the basis of the information, a conclusion is drawn as to the performed activities of the user.

A plausibility check is then carried out during which it is checked whether the works carried out by the user correspond to the activities specified in the process, i.e. whether the user has executed the process in the desired manner. If this is not the case, a negative feedback is sent to the user using the output 36.

Otherwise, the user receives a positive feedback.

Using the plausibility check, it is possible to detect error rates which are then stored in a memory along with information as to the working time determined by the control system 12, information of the vitality sensor system 40, and/or information of the environment sensor system. The memory may be located on the control system 12 itself or in an external computer. This data can serve to the documentation. An analysis of this data may be used to optimize the process performed and to improve the working conditions in that error rates are reduced.

The workwear unit 10 may also be used to control machines. To this end, the activities detected by the control system 12 are converted to instructions for the machine.

Figure 17:
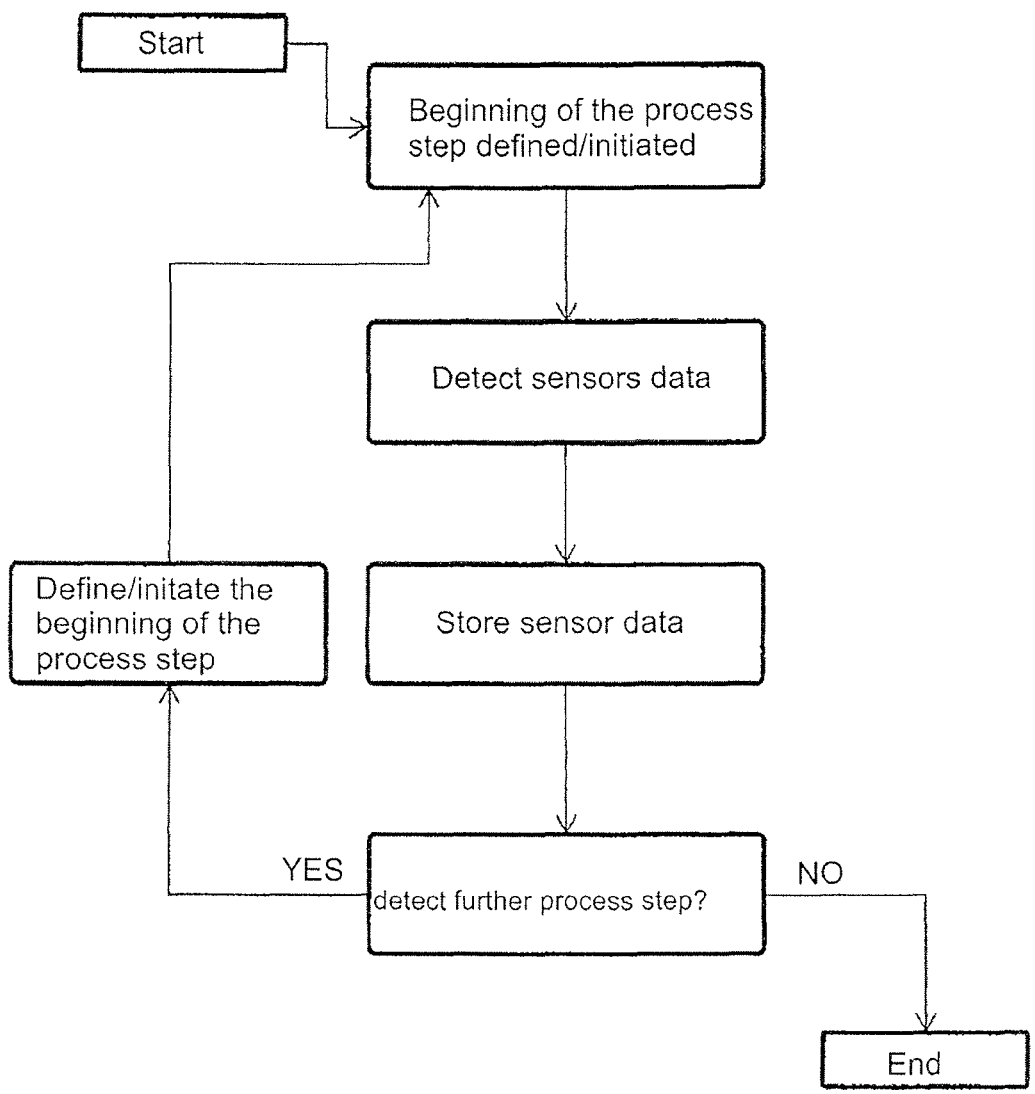
FIG. 17 shows a schematic overview of the method of teaching or inputting of process sequences.

FIG. 17 shows by way of example how exemplary processes can be stored in the workwear unit 10 ("teaching"). A processing step start is at first defined, for example by releasing the electrical release 48. The sensor data of the functional module 14 is then collected by the control system 12 and deposited in the memory. The process step is thus stored in the workwear unit 10. A further process step can then be started.

Although an embodiment of this invention has been disclosed, a worker of ordinary skill in this art would recognize that certain modifications would come within the scope of this disclosure. For that reason, the following claims should be studied to determine the true scope and content of this disclosure.

The invention claimed is:

1. A workwear unit for detecting, documenting, analyzing, monitoring and/or teaching processes comprising:
a portable control system;
at least one functional module connected with the portable control system, and which comprises at least a sensor module and a peripheral device; and
at least a glove and a bracelet associated with the glove, and wherein the glove fastens the portable control system and the functional module to a user's body, wherein the portable control system and the sensor module form a structural unit connected with the glove, wherein the sensor module has a barcode scanner fastened to the back of a hand, and wherein the peripheral device has an electrical release which is arranged outside on an index finger of the glove.

2. The workwear unit according to claim 1, wherein the sensor module, has a RFID reader, a RFID writer, a lacquer film thickness measuring device, a NFC reader, a motion sensor system, and/or an environment sensor system.

3. The workwear unit according to claim 1, wherein the bracelet has a socket for a plug, the socket resting on a dorsal side of a user's wrist with respect to a state placed on the wrist.

4. The workwear unit according to claim 3, wherein the bracelet has an output which is arranged on a radial and the dorsal side on the user's wrist in the state placed on the user's wrist.

5. The workwear unit according to claim 1, wherein the bracelet and the functional module are adapted to be electrically connected with each other by a connecting piece, the connecting piece being firmly connected with the functional module and being detachably connected with the bracelet via a plug, or the connecting piece being firmly connected with the bracelet and being detachably connected with the functional module via a plug.

6. The workwear unit according to claim 5, wherein the bracelet or the functional module and the plug have a plurality of contacts arranged in a contact pattern, wherein an electrical connection between the bracelet or the functional module and the plug being established via the contacts and the contact pattern being rotationally symmetrical through 180°.

7. The workwear unit according to claim 5, wherein the plug and/or the bracelet or the functional module have magnets which fasten the connecting piece to the bracelet or to the functional module.

8. The workwear unit according to claim 5, wherein the connecting piece has a bridge portion made of an elastic material which adjoins the plug and is configured in an undulated manner.

9. The workwear unit according to claim 8, wherein the bridge portion is configured such that the plug is prestressed against a plug-in direction.

10. The workwear unit according to claim 1, wherein the peripheral device is integrated into the glove, and/or the glove has a seat for the sensor module and the portable control system.

11. The workwear unit according to claim 10, wherein the peripheral device has a contact point via which an electrical connection with the portable control system is permitted.

12. The workwear unit according to claim 11, wherein the electrical release is arranged outside on an index finger of the glove.

13. The workwear unit according to claim 11, wherein the glove has conducting tracks which electrically connect the contact point with remaining peripheral devices.

14. The workwear unit according to claim 13, wherein the conducting tracks, the contact point, the antenna, the contact sensor and/or further components are made of conductive yarn, wire or strands which are sewed in the glove or enclosed by weaving.

15. The workwear unit according to claim 13, wherein, the conducting tracks, the contact point, the antenna, contacts of the electrical release, the contact sensor, the bend sensor and/or further components are printed on a foil which is integrated in the glove.

16. The workwear unit according to claim 10, wherein the peripheral device has at least one contact sensor which is located at a fingertip of the glove.

17. The workwear unit according to claim 10, wherein the peripheral device has an antenna which is located at a palm of a hand.

18. The workwear unit according to claim 10, wherein the peripheral device has a bend sensor which is placed on a finger of the glove.

19. The workwear unit according to claim 18, wherein the bend sensor is located on a side of a back of a hand on a finger of the glove and extends over a joint of a finger, the bend sensor being firmly connected with the glove only at an end facing the wrist.

20. The workwear unit according to claim 10, wherein the seat is a pocket into which the sensor module and the portable control system can be inserted and from which the sensor module and the portable control system can be withdrawn again, or in that the seat is a guide in which the sensor module and the portable control system can be pushed in and out.

21. The workwear unit according to claim 20, wherein the pocket or the guide is partly open such that a connecting portion of the sensor module can be plugged into the pocket or can be pushed into the guide.

22. The workwear unit according to claim 20, wherein the guide has two rails which delimit the guide in a transverse direction.

23. The workwear unit according to claim 22, wherein at one end of the guide, the rails are connected with each other by a termination, the termination delimiting the guide in a longitudinal direction.

24. The workwear unit according to claim 23, wherein the guide has a base plate which is fastened to the glove and from which the termination and/or the rails extend at an acute angle towards each other.

25. The workwear unit according to claim 24, wherein at least one peripheral contact which forms the contact point is provided at the pocket or at the rail at the base plate.

26. The workwear unit according to claim 25, wherein a sensor contact electrically connected with the peripheral contact is provided at the pocket or at the guide, and wherein the sensor contact is adapted to be connected with a continuous contact and the sensor module.

27. The workwear unit according to claim 10, wherein the sensor module and the portable control system can be fastened to the glove by the seat.

28. The workwear unit according to claim 27, wherein the sensor module has an output.

29. The workwear unit according to claim 1, wherein the electrical release is arranged in a region of a first phalanx of the index finger.

30. A workwear unit for detecting, documenting, analyzing, monitoring and/or teaching processes comprising:
a portable control system;
at least one functional module connected with the portable control system, and which comprises at least a sensor module and a peripheral device; and
a bracelet and at least one glove, wherein the glove is configured to fasten the portable control system and the functional module to a user's body, wherein the portable control system and the sensor module form a structural unit connected with the glove, and wherein the peripheral device has an electrical release that is arranged outside on a finger of the glove, and wherein the sensor module has a barcode scanner.

31. The workwear unit according to claim 30, wherein the barcode scanner is arranged on a finger of the glove.

32. The workwear unit according to claim 30, wherein the bracelet includes the portable control system and the glove includes the functional module.

33. The workwear unit according to claim 30, wherein the portable control system comprises a micro-computer, and wherein the functional module includes at least a RFID reader and contact sensors.

* * * * *